(12) United States Patent
Tumlinson

(10) Patent No.: US 8,908,189 B2
(45) Date of Patent: Dec. 9, 2014

(54) SYSTEMS AND METHODS FOR SWEPT-SOURCE OPTICAL COHERENCE TOMOGRAPHY

(75) Inventor: Alexandre R. Tumlinson, San Leandro, CA (US)

(73) Assignee: Carl Zeiss Meditec, Inc., Dublin, CA (US)

(*) Notice: Subject to any disclaimer, the term of this patent is extended or adjusted under 35 U.S.C. 154(b) by 272 days.

(21) Appl. No.: 13/444,410

(22) Filed: Apr. 11, 2012

(65) Prior Publication Data

US 2013/0100456 A1    Apr. 25, 2013

Related U.S. Application Data

(60) Provisional application No. 61/476,211, filed on Apr. 15, 2011.

(51) Int. Cl.
| | |
|---|---|
| *G01B 11/02* | (2006.01) |
| *G01B 9/02* | (2006.01) |
| *H01S 3/082* | (2006.01) |
| *H01S 5/14* | (2006.01) |
| *H01S 3/08* | (2006.01) |
| *H01S 3/105* | (2006.01) |
| *H01S 3/07* | (2006.01) |

(52) U.S. Cl.
CPC ............ *G01B 9/02091* (2013.01); *H01S 5/141* (2013.01); *H01S 3/0809* (2013.01); *G01B 9/02011* (2013.01); *G01B 9/02004* (2013.01); *H01S 3/105* (2013.01); *G01B 9/02082* (2013.01); *H01S 3/07* (2013.01); *G01B 2290/70* (2013.01); *H01S 3/0823* (2013.01); *G01B 9/02014* (2013.01); *H01S 3/08054* (2013.01)
USPC .......................................... 356/497; 356/479

(58) Field of Classification Search
CPC ........... G01B 9/02091; G01B 9/02014; G01B 2290/70; G01B 9/02011
See application file for complete search history.

(56) References Cited

U.S. PATENT DOCUMENTS

| | | | | |
|---|---|---|---|---|
| 3,849,001 | A | * 11/1974 | Inoue et al. | 356/327 |
| 3,932,039 | A | * 1/1976 | Frey | 356/138 |
| 5,173,743 | A | 12/1992 | Kim | |
| 5,877,856 | A | 3/1999 | Fercher | |
| 5,892,583 | A | 4/1999 | Li | |
| 6,366,390 | B1 | 4/2002 | King et al. | |

(Continued)

FOREIGN PATENT DOCUMENTS

EP    1154224 A1    11/2001

OTHER PUBLICATIONS

Invitation to Pay Additional Fees received for PCT Patent Application No. PCT/EP2012/056831, mailed on Oct. 8, 2012, 7 pages.

(Continued)

*Primary Examiner* — Tri T Ton
*Assistant Examiner* — Willie Merrell, II
(74) *Attorney, Agent, or Firm* — Morrison & Foerster LLP

(57) ABSTRACT

Systems and methods for increasing the duty cycle and/or producing interleaved pulses of alternating polarization states in swept-source optical coherence tomography (OCT) systems are considered. Embodiments including improved buffering, frequency selecting filter sharing among multiple SOAs, intracavity switching, and multiple wavelength bands are described. The unique polarization properties of the source configurations have advantages in speckle reduction, polarization-sensitive measurements, polarization state dependent phase shifts, spatial shifts, and temporal shifts in OCT measurements.

11 Claims, 10 Drawing Sheets

(56) References Cited

U.S. PATENT DOCUMENTS

| | | | |
|---|---|---|---|
| 6,847,449 B2 | 1/2005 | Bashkansky et al. | |
| 6,956,878 B1 | 10/2005 | Trisnadi | |
| 7,075,658 B2* | 7/2006 | Izatt et al. | 356/479 |
| 7,126,693 B2 | 10/2006 | Everett et al. | |
| 8,081,381 B2 | 12/2011 | Krasutsky | |
| 8,130,802 B2 | 3/2012 | Huber | |
| 2003/0020920 A1* | 1/2003 | Dave et al. | 356/479 |
| 2003/0210403 A1* | 11/2003 | Luscombe et al. | 356/491 |
| 2005/0213103 A1 | 9/2005 | Everett et al. | |
| 2008/0094613 A1* | 4/2008 | de Boer et al. | 356/73 |
| 2010/0245836 A1 | 9/2010 | Kulkarni et al. | |
| 2010/0265467 A1 | 10/2010 | Lescure et al. | |
| 2011/0051148 A1 | 3/2011 | Flanders et al. | |
| 2011/0080591 A1 | 4/2011 | Johnson et al. | |

OTHER PUBLICATIONS

Baumann et al., "Full Range Complex Spectral Domain Optical Coherence Tomography Without Additional Phase Shifters", Optics Express, vol. 15, No. 20, Oct. 1, 2007, pp. 13375-13387.

Baumgartner et al., "Resolution-Improved Dual-Beam and Standard Optical Coherence Tomography: A Comparison", Graefes Arch Clin Exp Ophthalmol, vol. 238, 2000, pp. 385-392.

Bilenca et al., "Numerical Study of Wavelength-Swept Semiconductor Ring Lasers: The Role of Refractive-Index Nonlinearities in Semiconductor Optical Amplifiers and Implications for Biomedical Imaging Applications", Optics Letters, vol. 31, No. 6, Mar. 15, 2006, pp. 760-762.

Chen et al., "High-Speed Wide Tuning Range Wavelength Swept Laser around 1310 Nm for Frequency Domain OCT", Proc. of SPIE, vol. 7280, 2009, pp. 72800A-1-72800A-8.

Choma et al., "Sensitivity Advantage of Swept Source and Fourier Domain Optical Coherence Tomography", Optics Express, vol. 11, No. 18, Sep. 8, 2003, pp. 2183-2189.

de Boer et al., "Determination of the Depth-Resolved Stokes Parameters of Light Backscattered from Turbid Media by Use of Polarization-Sensitive Optical Coherence Tomography", Optics Letters, vol. 24, No. 5, Mar. 1, 1999, pp. 300-302.

Goldberg et al., "200kHz A-Line Rate Swept-Source Optical Coherence Tomography with a Novel Laser Configuration", SPIE Conference 7889: Optical Coherence Tomography and Coherence Domain Optical Methods in Biomedicine XIV, paper 7889-55, Session 8, 2011, p. 117.

Götzinger et al., "High Speed Full Range Complex Spectral Domain Optical Coherence Tomography", Optics Express, vol. 13, No. 2, Jan. 24, 2005, pp. 583-594.

Hee et al., "Polarization-Sensitive Low-Coherence Reflectometer for Birefringence Characterization and Ranging", Journal of the Optical Society of America B, vol. 9, No. 6, Jun. 1992, pp. 903-908.

Hitzenberger et al., "Measurement and Imaging of Birefringence and Optic Axis Orientation by Phase Resolved Polarization Sensitive Optical Coherence Tomography", Optics Express, vol. 9, No. 13, Dec. 17, 2001, pp. 780-790.

Huber et al., "Amplified, Frequency Swept Lasers for Frequency Domain Reflectometry and OCT Imaging: Design and Scaling Principles", Optics Express, vol. 13, No. 9, May 2, 2005, pp. 3513-3528.

Huber et al., "Buffered Fourier Domain Mode Locking: Unidirectional Swept Laser Sources for Optical Coherence Tomography Imaging at 370,000 Lines/s", Optics Letters, vol. 31, No. 20, Oct. 15, 2006, pp. 2975-2977.

Jonathan, Enock, "Dual Reference Arm Low-Coherence Interferometer-Based Reflectometer for Optical Coherence Tomography (OCT) Application", Optics Communications, vol. 252, 2005, pp. 202-211.

Kuznetsov et al., "Compact Ultrafast Reflective Fabry-Perot Tunable Lasers for OCT Imaging Applications," Proc. of SPIE, vol. 7554, 2010, pp. 75541F-1-75541F-6.

Leitgeb et al., "Ultrahigh Resolution Fourier Domain Optical Coherence Tomography", Optics Express, vol. 12, No. 10, May 17, 2004, pp. 2156-2165.

Oh et al., "Wide Tuning Range Wavelength-Swept Laser With Two Semiconductor Optical Amplifiers", IEEE Photonics Technology Letters, Vol. 17, No. 3, Mar. 2005, pp. 678-680.

Park et al., "Real-Time Fiber-Based Multi-Functional Spectral-Domain Optical Coherence Tomography at 1.3 µm", Optics Express, vol. 13, No. 11, May 30, 2005, pp. 3931-3944.

Park et al., "In Vivo Burn Depth Determination by High-Speed Fiber-Based Polarization Sensitive Optical Coherence Tomography," Journal of Biomedical Optics, Vol. 6, No. 4, Oct. 2001, pp. 474-479.

Park et al., "Real-Time Multi-Functional Optical Coherence Tomography", Optics Express, vol. 11, No. 7, Apr. 7, 2003, pp. 782-793.

Potsaid et al., "Ultrahigh Speed 1050nm Swept Source / Fourier Domain OCT Retinal and Anterior Segment Imaging at 100,000 to 400,000 Axial Scans per Second", Optics Express, vol. 18, No. 19, Sep. 13, 2010, pp. 20029-20048.

Saxer et al., "High-Speed Fiber Based Polarization Sensitive Optical Coherence Tomography of in Vivo Human Skin", Optics Letters, vol. 25, No. 18, Sep. 15, 2000, pp. 1355-1357.

Schmitt et al., "Speckle in Optical Coherence Tomography", Journal of Biomedical Optics, vol. 4, No. 1, Jan. 1999, pp. 95-105.

Vergnole et al., "Artifact Removal in Fourier-Domain Optical Coherence Tomography with a Piezoelectric Fiber Stretcher", Optics Letters, vol. 33, No. 7, Apr. 1, 2008, pp. 732-734.

Wang et al., "Fourier Domain Optical Coherence Tomography Achieves Full Range Complex Imaging in Vivo by Introducing a Carrier Frequency during Scanning", Physics in Medicine and Biology, vol. 52, 2007, pp. 5897-5907.

Wang, Ruikang K., "In Vivo Full Range Complex Fourier Domain Optical Coherence Tomography", Applied Physics Letters, vol. 90, 2007, pp. 054103-1-054103-3.

Yasuno et al., "Simultaneous B-M-Mode Scanning Method for Real-Time Full-Range Fourier Domain Optical Coherence Tomography", Applied Optics, vol. 45, No. 8, Mar. 10, 2006, pp. 1861-1865.

Yun et al., "High-Speed Optical Frequency Domain Imaging", Optics Express, vol. 11, No. 22, Nov. 3, 2003, pp. 2953-2963.

Zotter et al., "Visualization of Microvasculature by Dual-Beam Phase-Resolved Doppler Optical Coherence Tomography", Optics Express, vol. 19, No. 2, Jan. 17, 2011, pp. 1217-1227.

International Search Report and Written Opinion received for PCT Patent Application No. PCT/EP2012/056831, mailed on Jan. 4, 2013, 12 pages.

* cited by examiner (a)

(b)

SYSTEMS AND METHODS FOR SWEPT-SOURCE OPTICAL COHERENCE TOMOGRAPHY

PRIORITY

This application claims priority to U.S. Provisional Application Ser. No. 61/476,211 filed Apr. 15, 2011, hereby incorporated by reference.

TECHNICAL FIELD

One or more embodiments of the present invention relate to the field of swept-source Optical Coherence Tomography (SS-OCT). In particular, the invention described herein provides systems and methods relating to high duty cycle swept-sources including embodiments to obtain interleaved sweeps of different polarizations. Several applications enabled by the invention are described.

BACKGROUND

Optical coherence tomography (OCT) is a cross-sectional, non-invasive imaging modality, that has application in diverse areas of medical imaging. In ophthalmology, OCT has been widely used for imaging the retina, choroid and anterior segment. Functional imaging of the blood velocity and vessel microvasculature is also possible. Fourier-domain OCT (FD-OCT) has recently attracted more attention because of its high sensitivity and imaging speed compared to time-domain OCT (TD-OCT) embodiment, which uses an optical delay line for mechanical depth scanning with a relatively slow imaging speed. The spectral information discrimination in FD-OCT is accomplished either by using a dispersive spectrometer in the detection arm (spectral domain or SD-OCT) or rapidly scanning a swept laser source (swept-source OCT or SS-OCT).

Compared to spectrometer-based FD-OCT, swept-source OCT (SS-OCT) has many advantages, including its robustness to motion artifacts and fringe washout, lower sensitivity roll-off and higher detection efficiency, etc. (see for example Choma et al. "Sensitivity Advantage of Swept Source and Fourier Domain Optical Coherence Tomography." Optics Express 2003 11(18): 2183-2189). Many different approaches have been implemented to develop high-speed swept sources, including semiconductor optical amplifier (SOA) based ring laser designs (see for example Yun et al "High-speed optical frequency-domain imaging" Opt. Express 11:2953 2003 and Huber et al "Buffered Fourier domain mode locking: unidirectional swept laser sources for optical coherence tomography imaging at 370,000 lines/s," Opt. Express 13, 3513 2005), and short cavity lasers (see for example Kuznetsov et al "Compact Ultrafast Reflective Fabry-Perot Tunable Lasers For OCT Imaging Applications," Proc. SPIE 7554:75541F 2010) among others. SOA based ring laser designs have been practically limited to positive wavelength sweeps (increasing wavelength) because of the significant power loss that occurred in negative tuning. This has been attributed to four-wave mixing (FWM) in SOAs causing a negative frequency shift in intracavity light as it propagates through the SOA (Bilenca et al "Numerical study of wavelength-swept semiconductor ring lasers: the role of refractive-index nonlinearities in semiconductor optical amplifiers and implications for biomedical imaging applications," Opt. Lett. 31: 760-762 2006)

A commercially available short cavity laser (Axsun Technologies Billerica, MA) in excess of 100 kHz has been reported (see for example Kuznetsov et al "Compact Ultrafast Reflective Fabry-Perot Tunable Lasers for OCT Imaging Applications," Proc. SPIE 7554: 75541F 2010). Short cavity lasers enable a significant increase in sweep speeds over conventional swept laser technology because the time needed to build up lasing from spontaneous emission noise to saturate the gain medium is greatly shortened (R. Huber et al "Buffered Fourier domain mode locking: unidirectional swept laser sources for optical coherence tomography imaging at 370,000 lines/s," Opt. Express 13: 3513 2005). However, the effective duty cycle of the bidirectional sweeping short cavity laser was limited to less than 50% because of the FWM effects mentioned above. The effective repetition rate of the laser is thus limited.

Several methods have been proposed to increase the effective repetition rates of SS-OCT systems including sweep buffering with a delay line, and multiplexing of multiple sources, thereby increasing the duty cycle of the laser. The method used to multiplex these sweeps together may include components that introduce orthogonal polarizations to the sweeps originating from different optical paths. Combining diverse polarizations at a polarization beamsplitter is a very light efficient way of transmitting the light to a single beam path.

Goldberg et al. demonstrated a ping-pong laser configuration for high-speed SS-OCT system that achieves a doubling of the effective A-line rate by interleaving sweeps of orthogonal polarization in the same cavity (see Goldberg et al "200 kHz A-line rate swept-source optical coherence tomography with a novel laser configuration" Proceedings of SPIE v.7889 paper 55 2011). This design is illustrated in FIG. 1. The paths from two semiconductor optical amplifiers SOAs were combined by a polarizing beam splitter (PBS) to generate light of orthogonal polarization states and are controlled precisely in time to double the effective duty cycle of the overall laser output. Each path has its own frequency selecting filter (101 and 102) for creating the swept sources. One path has a half waveplate to flip the polarization state of one path relative to the other. The output light is linearly polarized and only two-polarization states (horizontal and vertical as indicated by arrow 104 and circle 105) were demonstrated. The increased speed was used to acquire neighboring scans more quickly, with similar density to scans that would be acquired with a comparable speed had polarization diversity not been introduced.

Potsaid et al. demonstrated another method to double the effective repetition rate of a swept source laser by buffering and multiplexing the sweep of a single laser source (see Potsaid et al "Ultrahigh speed 1050 nm swept source/Fourier domain OCT retinal and anterior segment imaging at 100,000 to 400,000 axial scans per second" Opt. Express 18: 20029-20048 2010), as shown in FIG. 2. The laser sweep was split by a 60:40 fiber coupler and the original sweep from the 40 percent output side was directed to the 50:50 fiber coupler for multiplexing. A ~1 km length of fiber is used to delay the sweep from the 60 percent output by one half of the sweep period such that a "copy" of the sweep can be combined with the original sweep during the time period when the laser is off. Polarization controls are used to match the polarization states of the two sweeps. This doubles the repetition rate of the sweep at the outputs labeled 2 and 3 in FIG. 2.

However, the long fiber spool will cause a significant birefringence to the laser output. While the understanding of these particular methods to enhance speed of OCT acquisition has been appreciated, the use of these systems to provide enhancements to various types of OCT measurements has not.

It is an object of the present invention to provide improved systems capable of generating pulses of multiple polarization states at a high repetition rate. In addition it is an object of the present invention to make use of the unique polarization properties of these sources to improve several types of OCT measurements.

SUMMARY

The invention described herein provides systems and methods for improving swept-source OCT by increasing the duty cycle of the laser system and/or by generating pairs of interleaved pulses of orthogonal polarizations, arbitrary polarizations and dual-band, multi-band and wide-band sources. Further aspects of the invention include several enhancements to OCT measurements that are made possible using swept-source systems capable of generating interleaved pulses of different polarizations. These include speckle reduction, spatial and/or temporal separation between scanning beams, introduction of phase shifts, and polarization-sensitive measurements.

Three ways of increasing the duty cycle of the swept source system and or creating interleaved pulses of differing polarizations will be described in detail below. They include:
1. An improved buffering method to double the effective repetition rate of a swept source laser that minimizes birefringence compared to the long-fiber based buffering method previously described.
2. Laser cavity designs sharing a single filter between two (or more) SOAs.
3. Use of an intra-cavity optical switch in a laser cavity with a single semiconductor optical amplifier (SOA) and two wavelength scanning filters.

We can further extend the ideas of the invention to achieve swept sources with interleaved sweeps of two or multiple polarization states. Interleaved sweeps of orthogonal polarization are generated in several of the preferred embodiments of the invention for possible applications in polarization sensitive OCT. The initial polarization state of a laser output can be changed by use of waveplates and/or other polarization components. The light output from the source can be further divided into different branches with changed polarization states and then be combined together. In one of the embodiments of the dual-polarization swept source, fiber buffering along with the use of polarization components can be used to shift the laser sweep by a certain delay to generate multiple polarization states in a time sequence. Multi-polarization swept sources may be useful for polarization compounding, noise reduction or other applications in OCT imaging.

An additional aspect of the invention is to generate wide-band/dual-band/multi-band swept sources. By use of beam combiners/splitters, it is possible to couple multiple semiconductor optical amplifiers (SOAs) of different wavelength bands together. The wavelength bands can either be adjacent, resulting in a "wide-band" swept-source, or separated, producing a "multi-band" swept-source. Wide-band swept-source may find applications in ultra-high resolution OCT systems. Multi-band swept source may find applications for whole-eye imaging. For example, the operator may use the 840 nm or 1050 nm swept source band for retina imaging and switch to the 1310 nm band for anterior segment imaging in a real practice.

Furthermore the unique polarization properties of the source configurations described in the invention offer several advantages when applied to OCT measurements. OCT measurements are made with the interleaved pulses of orthogonal polarization states with detection such that each pulse corresponds to the collection of a single a-scan. The use of sequential orthogonal polarization states allow for the reduction of speckle noise contrast without substantially reducing spatial resolution. It also allows for the introduction of spatial or temporal separation between scanned beams. Interleaved pulses with orthogonal polarization states allow for the introduction of a relative phase shift between sample and reference arms in sequential a-scans allowing for complex conjugate free imaging or interleaved measurement of surfaces at different distances.

Embodiments of fiber-based polarization sensitive optical coherence tomography (PS-OCT) in the prior art used expensive polarization modulators to achieve alternating polarization states, which was a must for an unambiguous polarization sensitive measurement. We propose the use of a dual-polarization/multi-polarization swept source for PS-OCT. As the polarization state of the input laser switches between two (or more) adjacent sweeps, (at least) two sets of Stokes parameters can be obtained based on the complex depth encoded signals. Both the intensity images and the phase retardation can be calculated by comparing the Stokes vectors between the surface and deeper axial position. The use of a polarization modulator is no longer necessary, thus greatly simplifying and cost reducing a PS-OCT system design.

It is to be understood that both the foregoing general description and the following detailed description are exemplary and explanatory only and are not restrictive of the invention, as claimed.

DETAILED DESCRIPTION

The detailed description is divided into sections describing the various systems and applications related to interleaved pulses of multiple polarization states.

Improved Buffering Method

Figure 3:
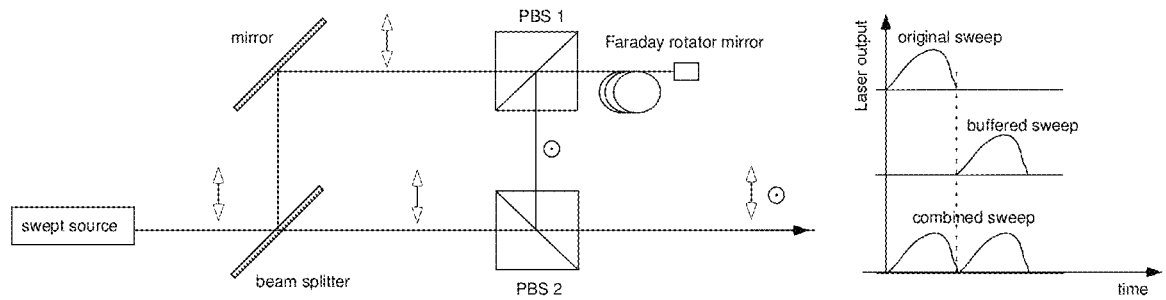
FIG. 3 shows one embodiment of an improved buffering technique of the present invention.

This section describes several novel embodiments for increasing the repetition rate and/or generating interleaved pulses of alternating polarization states in swept-source optical coherence tomography systems. FIG. 3 shows a novel buffering method of a dual-polarization swept source that doubles the repetition rate while providing interleaved pulses of orthogonal polarization states. The light from a conventional swept source laser is controlled to have a linear polarization state (assumed vertical in FIG. 3 without losing generality). The light gets split by a beam splitter. One portion of the beam passes straight through a polarizing beam splitter (PBS 2) and goes out. This portion of the beam has the original (vertical) linear polarization state and is called a copy of the "original sweep". Another portion of the beam is reflected by the beam splitter, hits the mirror, PBS 1, and is finally connected to a long fiber for buffering. A Faraday rotator mirror at the end of fiber is used to rotate the input polarization state by 90 degrees. The round-trip light propagation in long fiber with an orthogonal polarization state back cancels out the overall birefringence and generates a "buffered sweep". This "copy" of the sweep is then reflected by PBS1 and combined with the "original sweep" by PBS 2. The "buffered sweep" is combined with the original sweep during the time period when the laser is controlled to be "off". The overall repetition rate of the "combined sweep" has been doubled compared to the original sweep. The polarization states of the two sweeps are orthogonal to each other, and share the same axis in a Poincare sphere representation. A waveplate can be inserted into one arm to create interleaved pulses of the same polarization state while effectively doubling the repetition rate.

A quarter waveplate can also be used to achieve left circular or right circular polarization states for one sweep (such as the "original sweep" in FIG. 4), thus the two polarization states are orthogonal to each other in a Poincaré sphere representation, which is preferred in a fiber-based polarization sensitive OCT system for an unambiguous measurement, as will be discussed in detail in a later section. When the "original sweep" and the "buffered sweep" have different polarization states, we call the laser as a "dual-polarization swept source". The embodiment shown in FIG. 3 has the advantage of a single laser source.

Figure 1:
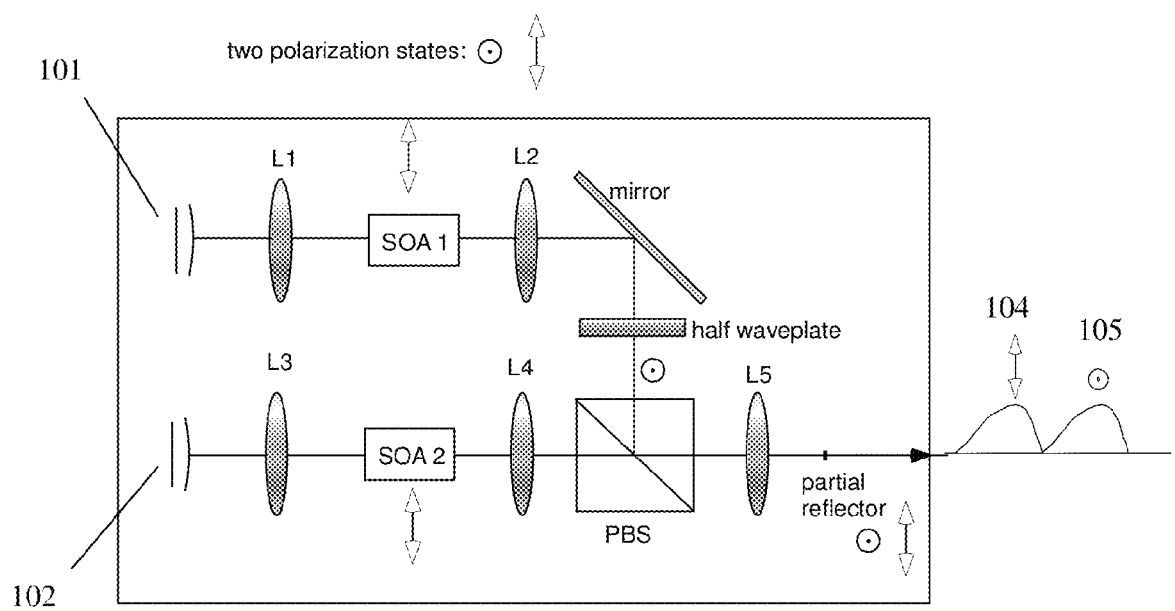
FIG. 1 shows a prior art swept-source capable of generating interleaved pulses of different polarizations at a high repetition rate.
Figure 2:
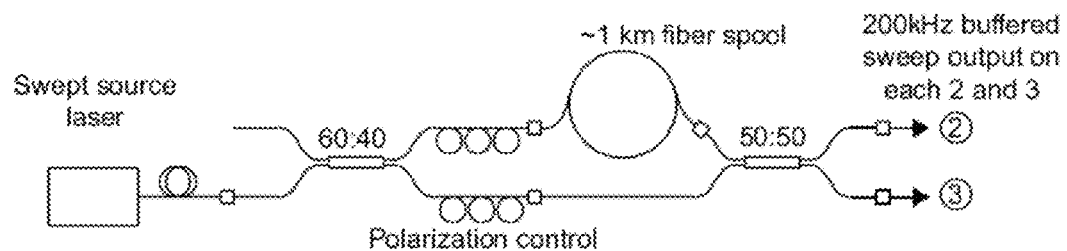
FIG. 2 shows a prior art swept-source system using fiber buffering to increase the effective repetition rate of the source.
Figure 4:
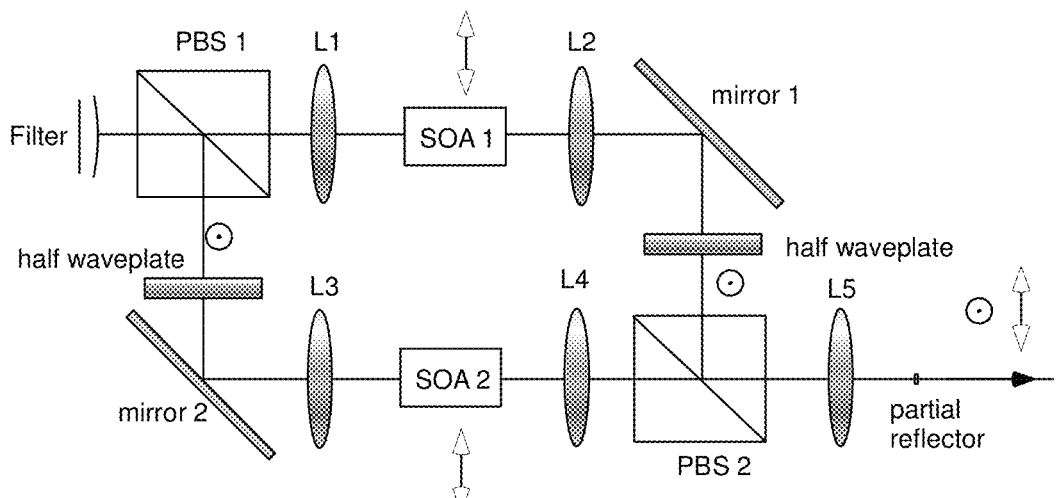
FIG. 4 shows an embodiment of the present invention in which a single filter element is shared between two SOAs to create interleaved pulses of differing polarization states.

Increased Duty-cycle or Interleaved Polarization States Using Single Frequency Selecting Filter with Multiple Sources FIG. 4 shows an additional embodiment of a dual-polarization swept source. This is similar to the Prior Art shown in FIG. 1 in that the light outputs from two SOAs are coupled together by two polarizing beam splitters (PBSs). In the embodiment shown in FIG. 4, two half waveplates are used to switch between vertical and horizontal (linear) polarization states. Unlike in the prior art example of FIG. 1, here the two SOAs share the same frequency selecting filter. This simplifies the overall complexity of the system because both laser paths, or branches, use identically the same filter, in essentially the same way, so that the direction of the wavelength shift is the same. Therefore both paths experience a forward sweep with high power and low noise at the same time, and both paths experience a reverse sweep with lower power and large noise due to four wave mixing effects at the same time. Here the two SOAs can be synchronized to be switched on in alternate cycles to enable interleaved orthogonal polarization states of the resulting pulse train. Because the unusable portion of the sweep occurs at the same time for both paths, no doubling of sweep rate is achieved in this embodiment. Two SOAs of orthogonal (linear) polarization states can be used to eliminate the need of two half waveplates and further simplify the overall design.

Figure 5:
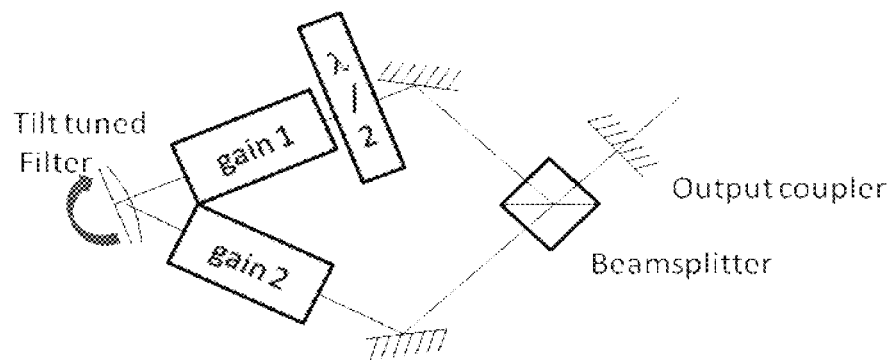
FIG. 5 shows an embodiment of the present invention in which a single filter element is shared between two SOAs to create interleaved pulses of differing polarization states and increase the repetition rate of the source.

An alternate embodiment that achieves a doubling of the duty cycle with a single frequency selecting filter shared between two gain elements is shown in FIG. 5. In this case, complementary wavelength sweeps in the multiple beam paths approach a reciprocating tilt tuned filter from different angles. When the filter angle (from normal incidence) is increasing in a first path, it is simultaneously decreasing in a second path; corresponding to optical frequency sweeps in opposite directions. The gain sections are alternately turned on when the sweep direction is favorable for power or noise characteristics. An optional half-waveplate can be introduced to rotate the polarization of one beam path relative to the other.

The tilt tuned filter may be a tilted Fabry-Perot wavelength selection filter, where more extreme angles away from normal incidence corresponds to decreasing selected wavelengths. It could be a grating filter where, when used in a Littrow configuration, a more extreme angle away from normal incidence corresponds to a longer selected wavelength. Gain media may correspond to semiconductor optical amplifiers, or any other gain media in which the gain is rapidly controllable. The beamsplitter may be any beam combining device. A dielectric polarizing beamsplitter cube as shown is only one example. Other polarization combining devices such as Wollaston prisms may also be used. Non polarizing beamsplitter may also be used. The device is shown with free space optics, however fiber coupled, or integrated optic solutions are similarly applicable. The same filter may be used for complementary sweeps, even if the two cavity paths form entirely separate laser cavities, i.e. if the beam combining occurs after the output coupler in each case.

This is substantially different from prior art (Oh et al "Wide tuning range wavelength-swept laser with two semiconductor optical amplifiers" IEEE Photonics Technology Letters 17(3): 678-680 2005) because in their case the tunable filter mechanism was inherently unidirectional. By selectively exciting the gain in the appropriate optical path, we use both directions of motion of the single filter to achieve pulses with unidirectional wavelength sweeping output with high duty cycle. Thus, for example, the system can be arranged so that the wavelength is increased during each pulse regardless of which of the two gain media are being excited.

Higher Duty Cycle Swept Source for OCT using an Intra-cavity Switch

Figure 6:
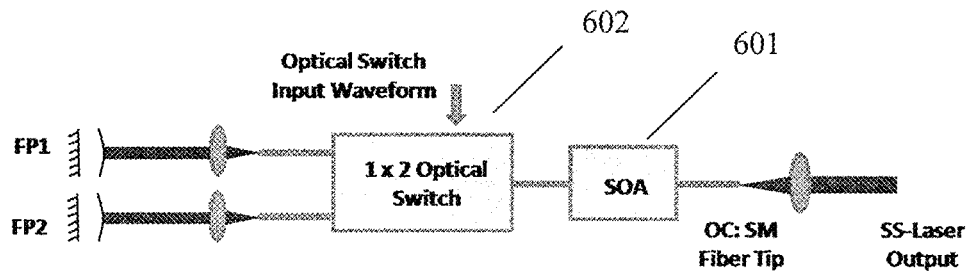
FIG. 6 shows an embodiment of the present invention in which an intracavity switch is used to increase the repetition rate.
Figure 6:
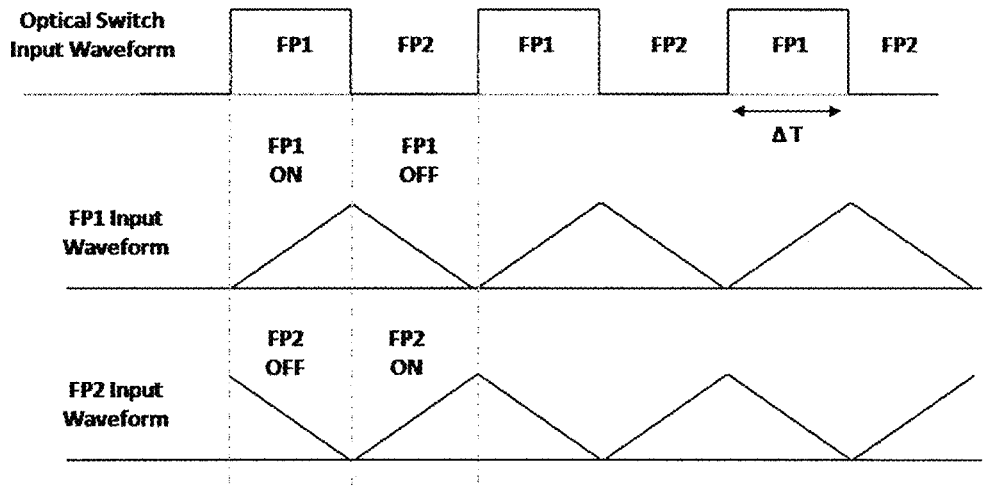

Another embodiment of the present invention uses an intra-cavity ultrafast optical switch, single semiconductor optical amplifier (SOA), and two Fabry-Perot (FP) filters to obtain increased duty cycle (>90%) wavelength swept source for OCT medical imaging applications. FIG. 6 shows the schematic of this embodiment. Effectively, this laser has a dual-cavity configuration and an ultrafast optical switch is used to make the switch between the two cavities. As shown in the input waveforms for FP filters and optical switch in the bottom of FIG. 6, the tuning of the two FP filters (180° out of phase) and intra-cavity optical switch is synchronized. Optical switching is used to switch alternatively between dual laser cavity configurations sharing the same gain element such that the effective laser cavity always experiences lasing in the preferential wavelength sweep direction for the best performance with regards to linewidth, power, and noise. Hence, the final output produces tunable wavelengths with 'unidirectional sweep' for the full duty cycle.

The proposed design in FIG. 6 uses a fiber pig-tailed SOA 601, and an optical switch. On one end of either of the laser cavity paths, or branches, are the FP minors. The right angle cleaved facet of the fiber may act as the output coupler. Lenses are used to collimate the fiber outputs. The design of the output coupler end may be changed depending on the requirements such as collimated output or fiber pigtailed output etc. This design can be made compact and only requires off-the-shelf components. One of the commercially available optical switches, Nanona (Boston Applied Technologies, Inc. Woburn, Mass.), which can be used for this purpose, has a compact housing (63×11×9 mm), ultrafast switching times (60 ns), low insertion loss, low cross-talk (<20 dB) and hence is an excellent candidate for use in this design. One of the current high-performance commercial SS laser (Axsun) operates at 100 kHz and 42% duty cycle. Using our design, one can double the scan rate to 200 kHz (sweep time: $\Delta T=5$ µs). The switching time of the commercially available switch is around 50 ns, and hence ~1% of the time for a single sweep. In principle, switching time of 50 ns can provide up to 90% duty cycle for SS laser operations at up to 1 MHz A-line rates. The performance of this laser can be improved further with future improvements in electro-optic technology. Overall, this laser design has the advantages of being a compact design, has improved performance at higher speed and higher duty cycle, and uses a single gain element (i.e. an SOA) to reduce costs of components.

In another embodiment of the invention, the laser design can be implemented by using free-space components instead of fiber pigtailed components. The end facets of the components may be angle cleaved and polished to avoid Fresnel reflections. The fiber tip at the other end of the cavity can act as an output coupler in this design.

Figure 7:
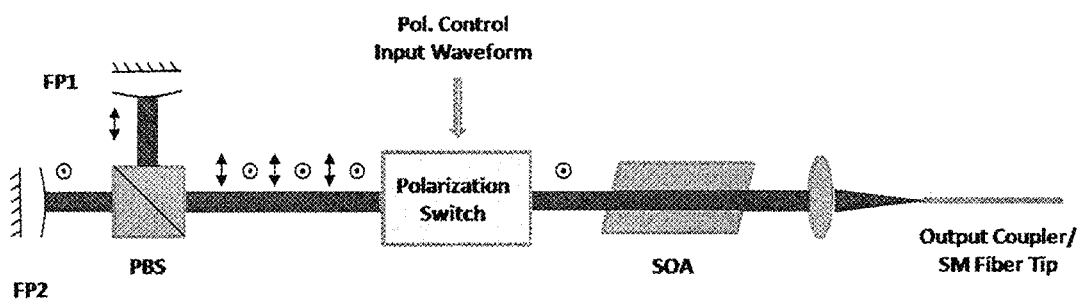
FIG. 7 shows an embodiment of an intracavity switch to achieve increased repetition rates and interleaved pulses of differing polarizations.

In another embodiment of the invention, the intracavity optical switch can be replaced by a polarization switching device to realize alternate dual-cavity configurations while using the same SOA to achieve higher duty cycle sweep operations as shown in FIG. 7. The output from a typical SOA based laser is highly linearly polarized because of the inherent polarization preference of the waveguides in SOA. Here, we replace the polarization insensitive optical switch with a polarization switch or controller as shown. The polarization controller switches the polarization of the incident light between two orthogonal polarization states. The polarization beam splitter (PBS) is used to direct light of a specific polarization (vertical or horizontal) to a given cavity path. The tuning of the two FP filters (180° out of phase) and intra-cavity polarization switch is synchronized similar to the previous scheme shown in FIG. 6. Hence polarization switching is used to switch alternatively between dual laser cavity configurations such that the effective laser cavity always experiences lasing in the preferential wavelength sweep direction for the best performance.

Figure 8:
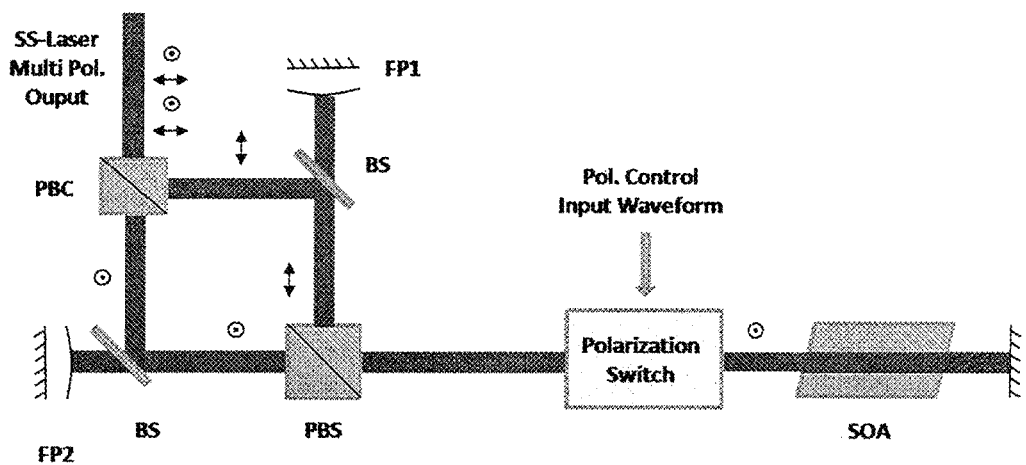
FIG. 8 shows a second embodiment of an intracavity switch to achieve increased repetition rates and interleaved pulses of differing polarizations.

In yet another embodiment of the invention, dual-polarization interleaved output can be obtained as shown in FIG. 8. In this laser configuration, two effective cavities exist depending on the polarization state of the laser. Both ends of each cavity can be high reflective mirrors as the power is coupled out of the laser cavities using beam splitters (BS). The light coming out of the SOA is linearly polarized (i.e. horizontally polarized). The polarization controller inside the cavity can be used to switch the light into horizontal and vertical polarizations in alternate sweep cycles. The polarization beam splitter (PBS) splits the orthogonally polarized light into two cavity paths depending on the polarization state. The tuning of the two FP filters (FP1 and FP2, 180° out of phase) and intra-cavity polarization switch is synchronized similar to the previous designs shown in FIGS. 6 and 7 to create a train of interleaved pulses. Hence polarization switching is used to switch alternatively between the dual laser cavity configurations with the difference being that the laser output light is tapped out by using polarization insensitive (i.e. partial reflecting) beam splitters (BS) and the output from the two paths are combined using a polarization beam combiner (PBC) for efficient coupling. In a slightly different design, one of the ends of the SOA could act as a mirror if it is cleaved and polished at right angle and a highly reflective coating or mirror surface can be attached to it. In another embodiment of the invention, wavelength selection filters could act as output couplers and the output from each filter can later be recombined by using polarization beam combiners. Although embodiments of the present invention are discussed herein with respect to the wavelength selection filter being a FP filter, one skilled in the art could imagine additional embodiments of the invention that are not limited to this configuration. There are several advantages of using a multi-polarization interleaved output from a SS laser as will be described in further detail below.

Advantages of the intracavity switch approach include: a) higher duty cycle >90% operation using 'unidirectional sweeping' SS laser, b) a single gain element (SOA) is used compared to two gain elements used in previous solutions resulting in cost reduction as SOAs are one of the most costly components in a SS laser, c) easy to align, compact design with high performance, and d) low intra-sweep variations because same gain element is used for either cavity.

Multiple Polarization Swept-Sources

Figure 9:
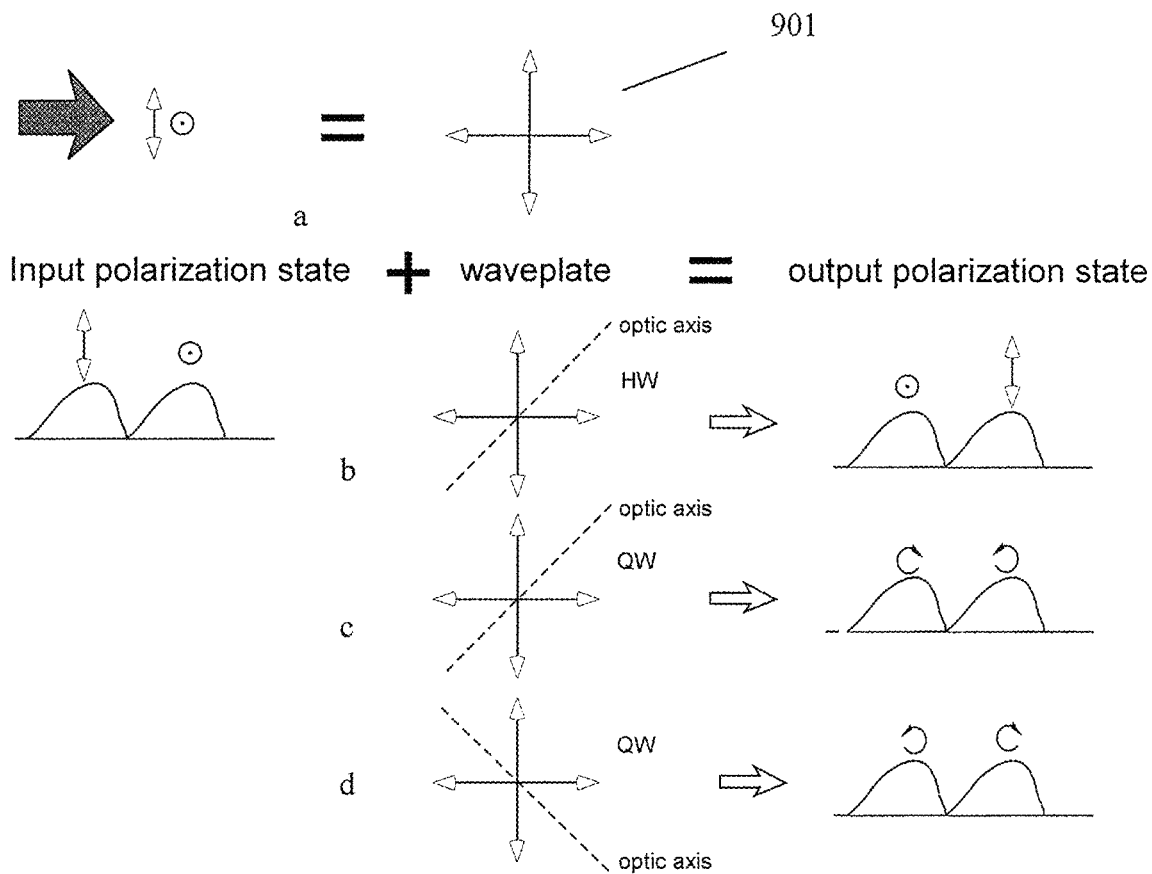
FIG. 9 illustrates the effect of a variety of waveplates on the polarization states of two laser pulses of differing initial polarizations.

The dual polarization concepts described in the previous sections can be further extended to achieve multi-polarization swept sources. As was mentioned above, the initial polarization state can be changed by use of waveplates or other polarization components. FIG. 9 shows how the input polarization states can be changed by the use of various types of waveplates. Assuming the initial dual-polarization swept source has a vertical linear polarization state for the first sweep and horizontal (perpendicular to the paper plane) for the second sweep, as shown in FIG. 9(a). If the observer is looking from the left, the two linear polarization states look like a "cross" 901, vertical for the first sweep and horizontal (left to right) for the second sweep. If a half waveplate (HW) is used with its optic axis aligned 45° to both of the two polarization states (FIG. 9b), the output polarization states changes to horizontal for the first sweep and vertical for the second sweep. Similarly, if a quarter waveplate (QW) is used, circular polarization states can be achieved as shown in FIGS. 9c-d. The direction of circularly polarized light depends on the orientation of the waveplate.

The waveplates can be aligned with different angles to achieve other different polarization states, such as tilted linear polarization or elliptical polarization. Also, ⅛ waveplate or any other waveplate, attenuator, retarder, optical rotator, polarization controller, polarization changer can also be used.

Figure 10:
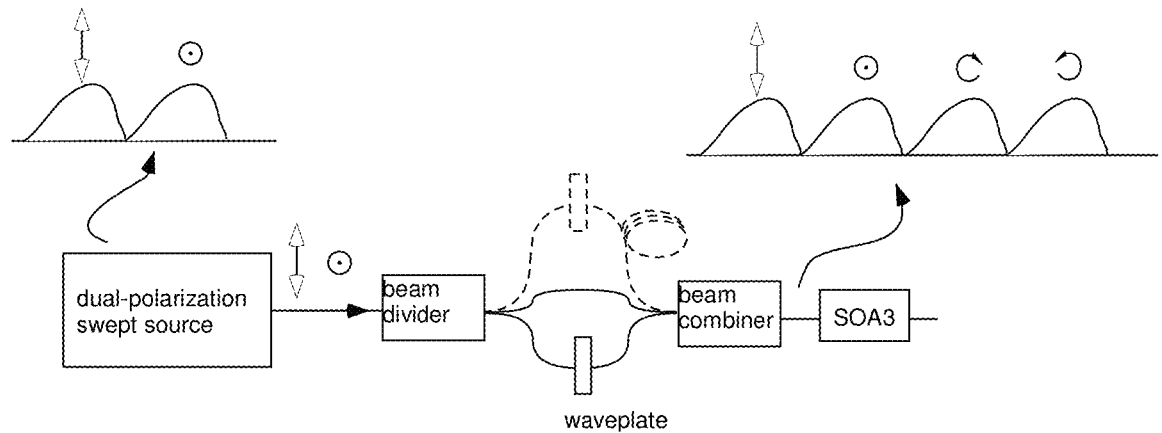
FIG. 10 shows an embodiment of the present invention capable of generating interleaved pulses of more than two differing polarization states.

The light from the swept source can be divided into different branches with changed polarization states and then be re-combined together. Fiber buffering can be used to shift the laser beam on the order of a few sampling intervals to avoid coherent interference between light of different polarization states from multiple fiber branches, or to shift the whole sweep (spectra) by a significant delay to generate different polarization states in a time sequence. FIG. 10 shows a swept-source laser embodiment to generate multiple polarization states. The components of this embodiment include:

1. The output of a single dual-polarization swept source goes to a beam divider
2. The beam divider separates the beam to different branches
3. Waveplate(s) are used in a single branch to alter the input polarization state to a different polarization state. (Different waveplate will affect the input light differently, as illustrated in FIG. 8)
4. Fiber based buffering can be used to delay the light in any branch
5. A beam combiner is used to combine lights from different branches
6. A third SOA (SOA 3 in FIG. 9) can be used as a booster amplifier to further amplify the power, or to optimize the spectrum shape of the laser output.

Alternatively, two or more dual-polarization (or single-polarization) lasers of different polarization states can be directly combined.

Wide-band, Dual-band or Multi-band Swept Source

This section describes various embodiments relating to the creation of wide-band, dual-band or multi-band swept sources. By use of beam combiners/splitters, it is possible to couple multiple semiconductor optical amplifiers (SOAs) of different wavelength bands together. The wavelength bands can either be adjacent, resulting in a "wide-band" swept-source, or separated, producing a "multi-band" swept-source. Wide-band swept-source may find applications in ultra-high resolution OCT systems. Multi-band swept source may find applications for whole-eye imaging. For example, the operator may use the 840 nm or 1050 nm swept source band for retina imaging and switch to the 1310 nm band for anterior segment imaging in a real practice.

Figure 11:
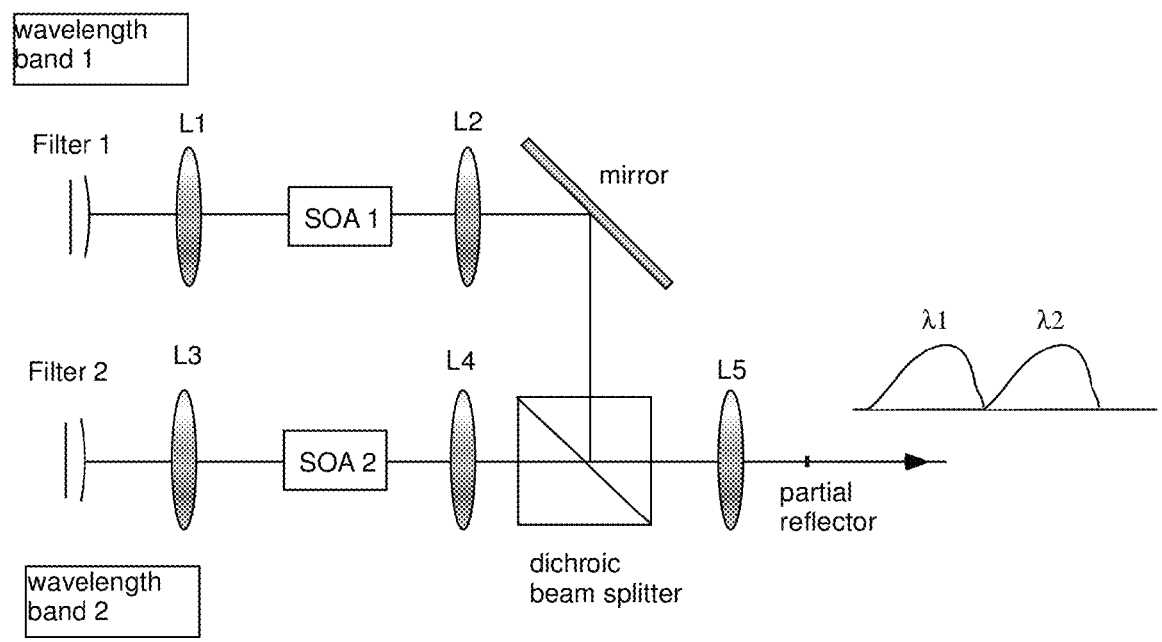
FIG. 11 shows an embodiment of the present invention in which two SOAs of differing wavelength bands are interleaved to create a dual band swept-source.

FIG. 11 shows an embodiment for a wide-band/dual-band/multi-band swept source laser:

1. Two broadband SOAs have different center wavelengths, such as one centered at 840 nm and the other at 870 nm, or one at 1310 nm and the other at 1050 nm, etc. Different center wavelengths can be used/combined to address different applications.
2. The dichroic beam splitter transmits the wavelength band for SOA2 and reflects the wavelength band for SOA 1.
3. More than two different wavelength bands can be coupled if additional dichroic beam splitter(s) are used.
4. If the center wavelengths of the two SOAs are close, the spectra (bands) of the two SOAs can be combined to achieve one wide-band source, where the polarization states of the two SOAs can be the same.

Figure 12:
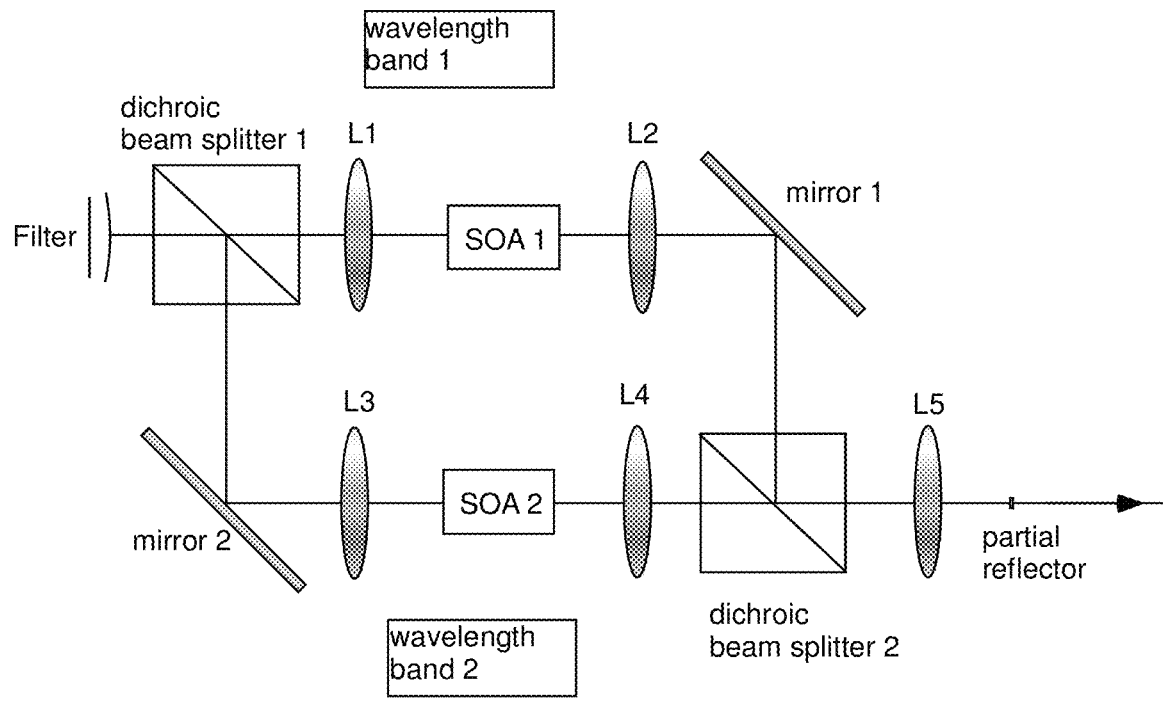
FIG. 12 shows an embodiment of the present invention in which two SOAs of differing wavelength bands are interleaved to create a dual band swept-source using a single filter element.
Figure 13:
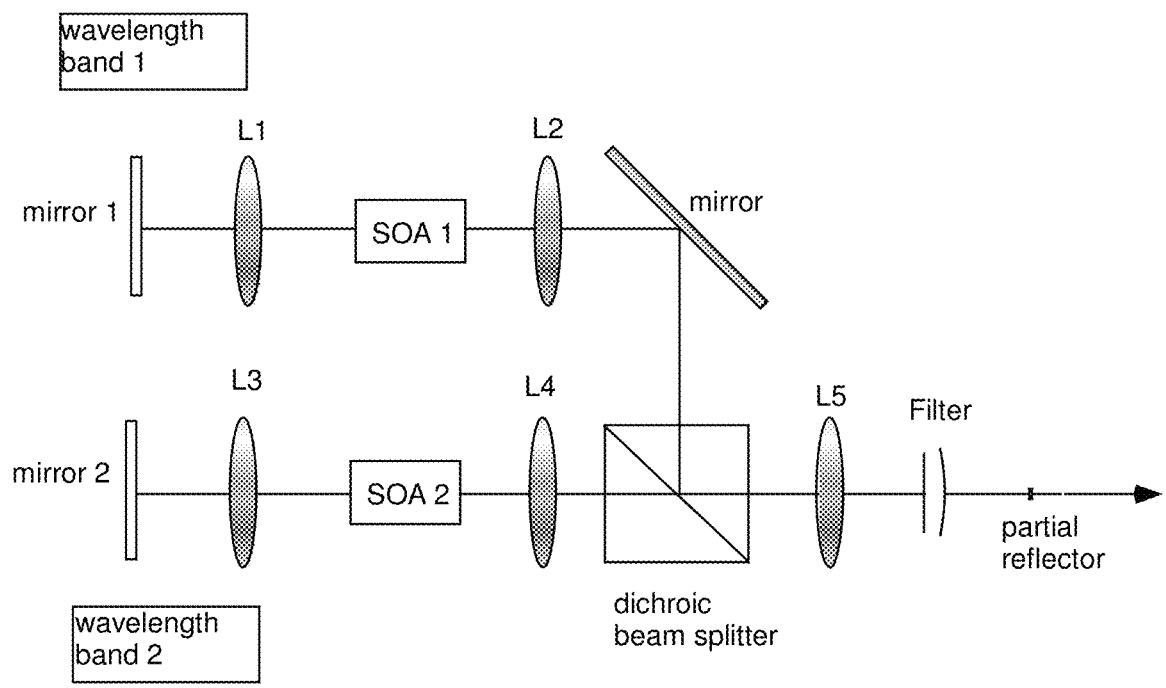
FIG. 13 shows another embodiment of two SOAs of differing wavelength bands being interleaved to create a dual band swept-source using a single filter element.

FIGS. 12 and 13 show additional embodiments where two (multiple) SOAs share the same spectral filter in the cavities. Two dichroic beam splitters are used in FIG. 12. Specifically, dichroic beam splitter 1 transmits wavelength band 1 for SOA 1 and reflects wavelength band 2 for SOA 2. While dichroic beam splitter 2 transmits wavelength band 2 for SOA2 and reflects wavelength band 1 for SOA 1. While FIG. 12 shows the use of a spectral filter in a retro-reflection mode, FIG. 13 shows another embodiment where a spectral filter is used inside the laser cavity in a transmission mode. Two minors are used at the ends of the laser cavities.

Other beam combiner/splitters can also be used to design a wide-band or multi-band swept source. Other beam combiners/splitters include but are not limited to grating, prism, hot/cold minor, volume Bragg grating, holographic beam combiner, etc. Those skilled in the art can readily devise other varied embodiments based on different beam combiners/splitters.

Applications of Interleaved Pulses of Differing Polarization States in SS-OCT

Figure 14:
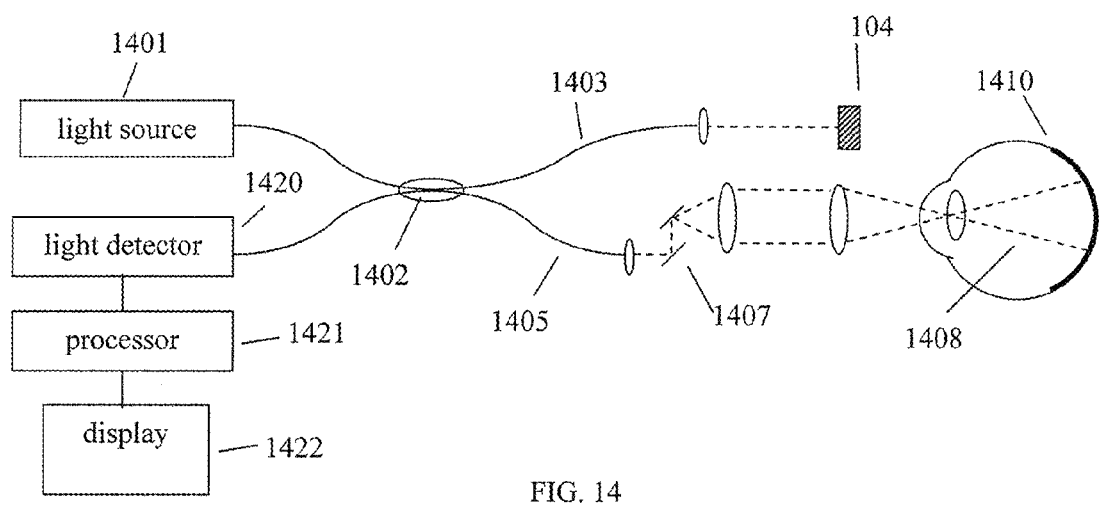
FIG. 14 shows the basic components of an SS-OCT system.

The remaining sections are focused on applications of interleaved pulses of different polarizations for swept-source optical coherence tomography (SS-OCT). An SS-OCT scanner, illustrated in FIG. 14 includes a swept-light source. Light from the source 1401 is routed, typically by optical fiber 1405, to illuminate the sample 1410, a typical sample being tissues in the human eye. The light is scanned, typically with a scanner 1407 between the output of the fiber and the sample, so that the beam of light (dashed line 1408) is scanned laterally (in x and y) over the area or volume to be imaged. Light scattered from the sample is collected, typically into the same fiber 1405 used to route the light for sample illumination. Reference light derived from the same source 1401 travels a separate path, in this case involving fiber 1403 and retro-reflector 1404. Those skilled in the art recognize that a transmissive reference path can also be used. Collected sample light is combined with reference light, typically in a fiber coupler 1402, to form light interference in a detector 1420. The output from the detector is supplied to a processor 1421. The light detector could comprise a single photodetector or a balanced detection scheme. The results can be stored in the processor or displayed on display 1422. The Fourier transform of the interference light reveals the profile of scattering intensities at different path lengths, and therefore scattering as a function of depth (z-direction) in the sample (see for example Leitgeb et al, "Ultrahigh resolution Fourier domain optical coherence tomography," *Optics Express* 12(10):2156 2004). The profile of scattering as a function of depth is called an axial scan (A-scan). A set of A-scans measured at neighboring locations in the sample produces a cross-sectional image (tomogram or B-scan) of the sample. A collection of B-scans makes up a data cube or cube scan.

For the discussion of speckle reduction, spatial and temporal separation and phase shifts, any source capable of generating interleaved pulses of orthogonal linear polarization can be used while the PS-OCT discussion is limited to interleaved pulses capable of creating orthogonal pulses in a Poincaré sphere representation. In the most general sense, pulses of broadband illumination with interleaved orthogonal polarization may be created by combination of two beams with orthogonal polarization states at a passive beam combiner.

Speckle Reduction

Speckle is a phenomenon of imaging with coherent waves which results in image structure that does not relate in a directly interpretable way to sample structure. It is caused by the interference of scattered waves from multiple, randomly placed, elements at distances less than the resolution of the system. The appearance of speckle is a high contrast, granular, 'bubbly', overlay of the information of real interest in the image. Although speckle may carry statistical information about the sample, in medical imaging speckle is distracting as it may be difficult for a clinician to distinguish between real tissue structures and imaging artifacts.

Speckle reduction is typically performed by combining image data with uncorrelated speckle patterns. Methods to reduce the speckle correlation in optical coherence tomography are primarily one of spatial, angular, spectral, or polarization compounding. Spatial compounding is most common in practice, and combines information from nearby locations whose distance is greater than the correlation length, such that speckle are decorrelated—which results in significant loss of spatial resolution. Polarization compounding involves the collection of two tomograms produced with orthogonal polarization, such that their speckle is at least partially uncorrelated with each other and therefore reduce the magnitude of speckle in an averaged tomogram by a maximum of the square root of two. Because the tomograms can be directly superimposed spatially, there is no inherent loss of spatial resolution. Polarization compounding has not been widely implemented because the magnitude of speckle reduction is modest, and because the methods to implement it are historically relatively expensive, such as active components to modulate polarization or duplication of detection mechanisms to measure orthogonally split polarizations.

Figure 15:
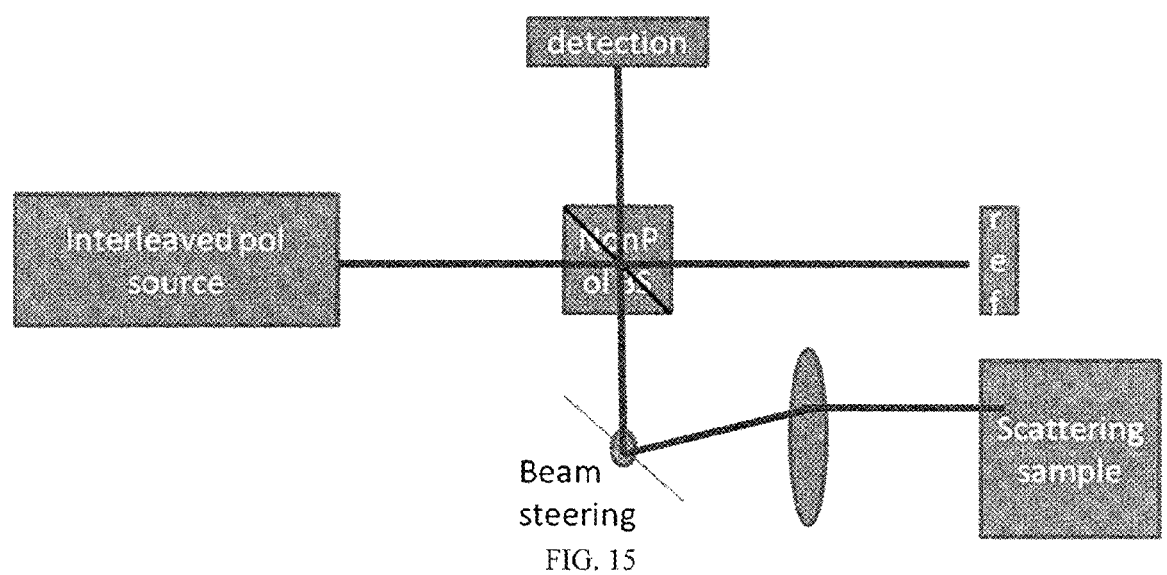
FIG. 15 shows an SS-OCT system using a source capable of producing interleaved pulses of varying polarizations states.
Figure 16:
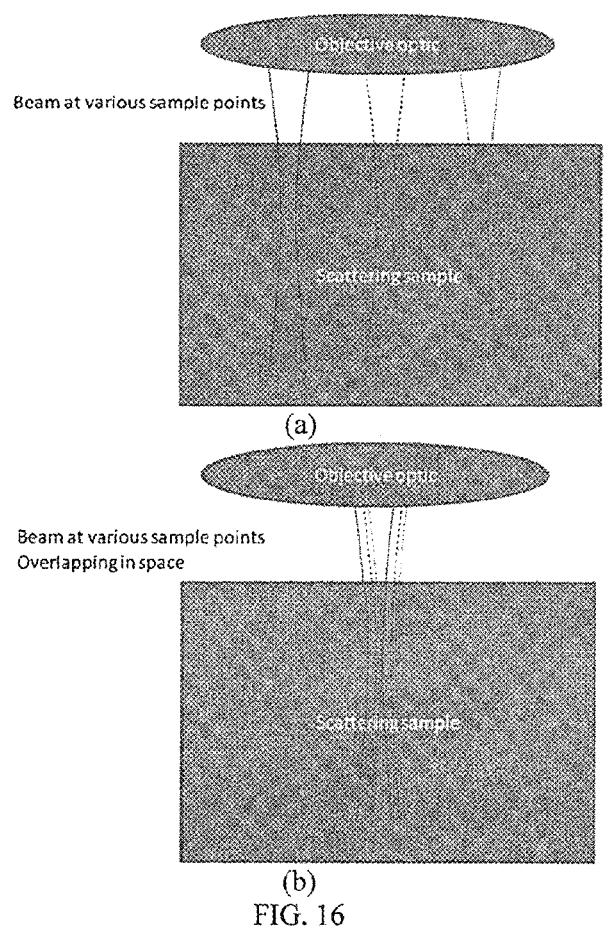
FIG. 16 shows how SS-OCT with polarization interleaved pulses can be used to reduce speckle.

According to Schmidt (Schmitt et al "Speckle in Optical Coherence Tomography", J. Biomed. Opt. 4:95 1999), the speckle patterns created by orthogonal polarizations are at least partially decorrelated, and in particular the components related to multiple scattering may be highly decorrelated. A SS-OCT system, illustrated in FIG. 15, can used to probe a sample as described in FIG. 16, to take advantage of polarization diversity for speckle reduction. FIG. 15 shows an SS-OCT apparatus consisting of broadband light source producing interleaved pulses of orthogonal polarization, an interferometer including a reference arm and a sample arm containing a scattering sample, optically combined by a non-polarizing beamsplitting device. Optionally the sample arm may contain a beam steering apparatus such as a galvanometer mirror to scan the light over the scattering sample.

FIG. 16(a) and (b) shows the width of a beam of light such as may be used to probe the volume of a scattering sample in optical coherence tomography in two different sampling configurations. The beams associated with three sequential samples (a-scans) may be well separated as in FIG. 16(a), or substantially overlapping as in FIG. 16(b). The degree of speckle correlation between adjacent scans depends on the degree to which they share common information. The scans in 16(a) do not have any overlap in their cross sections and their speckle are uncorrelated regardless of their polarization. Averaging theses scans would reduce speckle, but would also reduce spatial resolution. In the case of FIG. 16(b), the beams have a significant overlap. If they share the same polarization their speckle information is correlated. Averaging theses scans would do very little to reduce speckle, and would likewise not reduce spatial resolution much. If they have alternating orthogonal polarizations, directly adjacent scans would be less correlated—so averaging would reduce the speckle contrast in the image, and introduce very little loss of spatial resolution. The spacing of the sequential samples should not be greater than the lateral correlation length (or the approximate speckle dimension / beam width). If the samples are spaced at a distance greater than the lateral correlation length, the speckle will be decorrelated anyway, regardless of polarization and therefore the polarization diversity is of no consequence. The algorithm to produce a speckle reduced tomogram from the two polarization states may include averaging, taking the greater of the two orthogonal values, or taking a weighted statistical estimator from neighboring measurements of identical and orthogonal polarization states.

Spatial and Temporal Separation

Dual beam OCT, which scans a single target with multiple beams of light was described by Fercher (see for example U.S. Pat. No. 5,877,856) using a Wollaston prism to achieve dual beams of split polarization from a single linear input polarization state aligned at approximately 45 degrees to the birefringent axis of the Wollaston prism. He disclosed a method to measure the beams independently by passing the light through a polarization splitter and on to a pair of detectors. A similar dual beam effect was later realized by Zotter et al, (see for example Zotter et al "Visualization of microvasculature by dual-beam phase-resolved Doppler optical coherence tomography" Opt Express 19(2):1217-27 2011) by nearly complete duplication of the systems for each angle and combination with a small angle offset at beamsplitting device.

The method described below simplifies the dual measurement methods in the prior art by acquiring the data serially in an interleaved rather than fully parallel manner. The interleaved measurements can use the same optical path, detectors and detection electronics while retaining the advantages of a dual beam method. For the purpose of calculating maximum permissible exposure, the power is split to spatially distinct locations allowing roughly a doubling of allowable total average power incident on the sample. The time between sequential axial scans is very short compared to the time separation between well separated beams, which can be tens or hundreds of sample spacings away. Sequential scans can then be considered simultaneous for the purpose of calibrating out motion of the sample that occurs during a full length transverse scan containing hundreds of axial scans. A constant and well defined temporal offset is still introduced between a first scan and a second scan such as for Doppler measurement.

Figure 17:
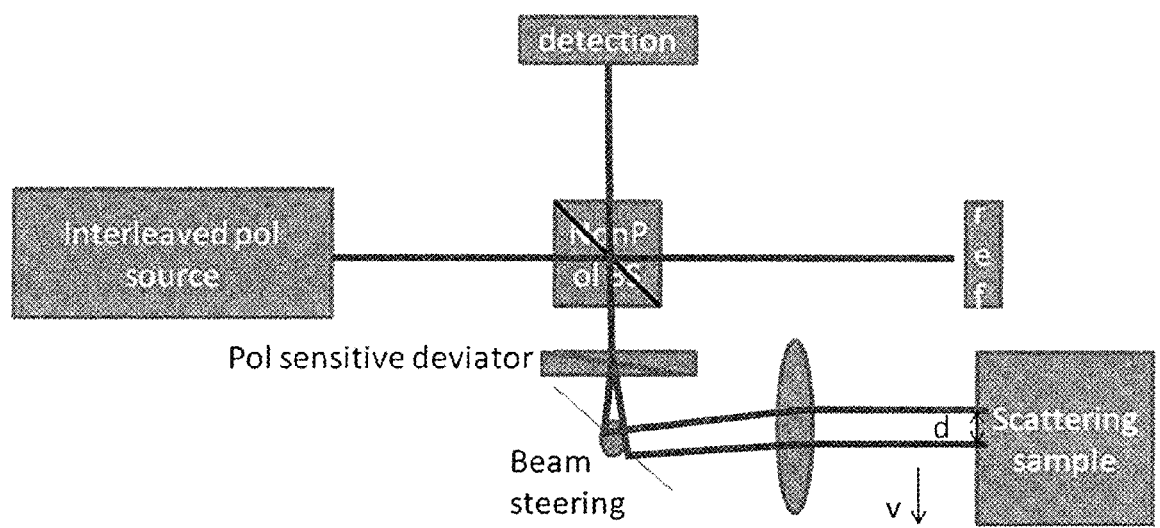
FIG. 17 shows how a polarization sensitive element in an SS-OCT system with interleaved pulses of varying polarization states can be used to achieve spatial or temporal separation in a scattering sample.

The orthogonal polarization of temporally sequential a-scans may be used to introduce a positional offset between the beams as they contact the sample. For example a passive polarization sensitive component such as a Wollaston prism may introduce an angular deviation that is different for beams of orthogonal linear polarization. If such a prism is introduced in a scanning system, near a pupil of the system, the result is a lateral displacement of the measurement beam in the sample. FIG. 17 shows an embodiment of this aspect of the invention. Here an optical coherence tomography apparatus includes a source producing interleaved pulses of orthogonal polarization, an interferometer including a reference arm, a sample arm containing a scattering sample, wherein the reference and sample arms are optically combined by a non-polarizing beamsplitting device, a beam steering device to scan the light over the scattering sample, and a passive polarization sensitive device, such as a Wollaston prism, which deflects the beams according to their polarizations in addition to the amount of scan deflection introduced by the beam steering device. The displacement due to polarization difference is labeled d on the scattering sample. If the deviation because of polarization is introduced in the scanning direction, the same position will be scanned twice; the spatial separation on the target 'd' translates to a temporal separation 't'=d/v where v is the scan velocity across the target.

The size and direction of the lateral displacement desired depends on the application. A small displacement may be introduced such that the displacement counteracts the displacement of a constant velocity scan mechanism during the period between a-scans. Thus temporally sequential a-scans occur in pairs that are substantially overlapping at the same point in space. Another application might be to produce a wide enough separation such that the beams may be considered independently for thermal hazard in a Maximum Permissible Exposure calculation. Another application is to separate the beams to introduce a specific temporal delay between the two measurements for the purpose of a change measurement over a precise time period, such as for Doppler velocity determination. Another application of recording beams offset in position relative to each other is to compensate the effect of sample motion on an object. In this case, if at least one point in the scan is effectively measured twice, it is possible to calculate the average axial velocity of the scanned object from the displacement of the point between the two recordings.

Phase Shifts

Methods to periodically modulate the phase of the interference between the sample and reference have been shown. The physical length of an arm of the interferometer may be rapidly changed by a short, relatively fixed amount, such as by placing the reflective element on an oscillating piezoelectric mount (see for example Wang et al "Fourier domain optical coherence tomography achieves full range complex imaging in vivo by introducing a carrier frequency during scanning" Physics in Medicine and Biology 52(19): 5897 2007), or by stretching a length of fiber (see for example Vergnole et al "Artifact removal in Fourier-domain optical coherence tomography with a piezoelectric fiber stretcher" Optics Letters 33(7): 732-734 2008). Also the optical path length may be modulated by temporally changing the optical index of refraction of an element in that path, such as by subjecting an electro optic crystal to a voltage (see for example Gotzinger et al "High speed full range complex spectral domain optical coherence tomography" Optics Express 13(2): 583-594 2005). Multiple path length reference arms have been described by Li (see for example U.S. Pat. No. 5,892,583) for the measurement of details at different depths within a scattering target.

A solution utilizing polarization diversity to achieve two different path lengths in the interferometer avoids the need for an active component in the difference path of the interferometer. A solution where a small, relatively fixed phase difference is added passively by a waveplate has the advantages of being extremely stable. A solution using polarization splitting to divide the reference into two paths of arbitrary length has the advantage over other beamsplitting methods in that it can be very light efficient while using the same spectral band. If both polarizations were input to the system simultaneously, they could be read differentially by a pair of detectors each responding to a different polarization state. Sequential polarization states in the input allow both polarizations to be read by the same detectors in serial fashion. Using a polarization modulator after the source is potentially costly and adds complexity to the system. The current solution of a source using passive polarization combining of two optical paths having orthogonal polarization states is advantageous because the two polarization states may be achieved at lower cost, and may be available as a side effect of a source configuration designed primarily to achieve high duty cycle and high optical efficiency.

Figure 18:
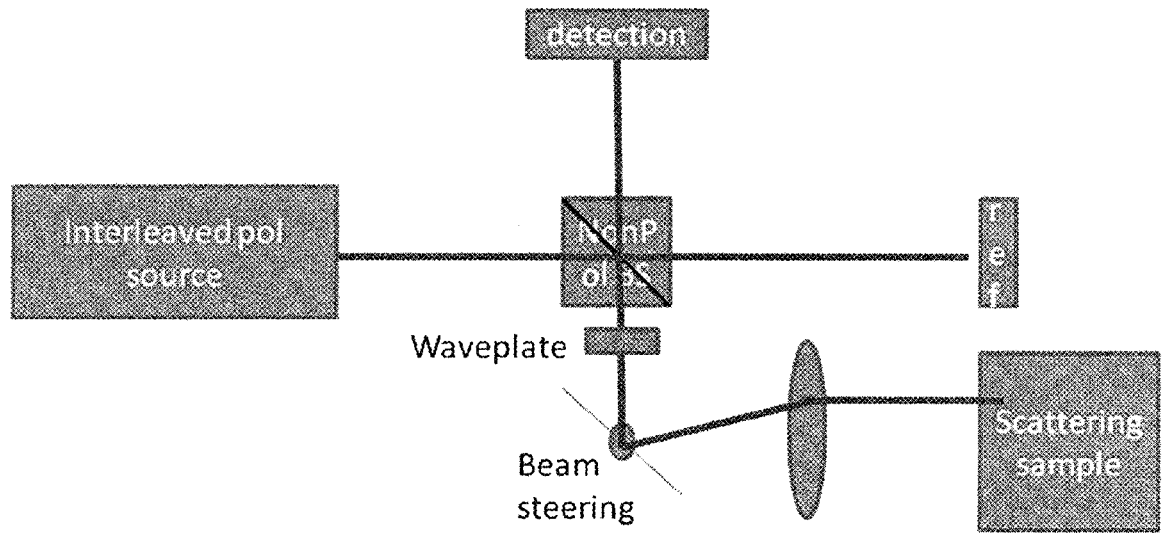
FIG. 18 illustrates how phase shifts can be introduced in a SS-OCT system using interleaved pulses of differing polarization states.
Figure 18:
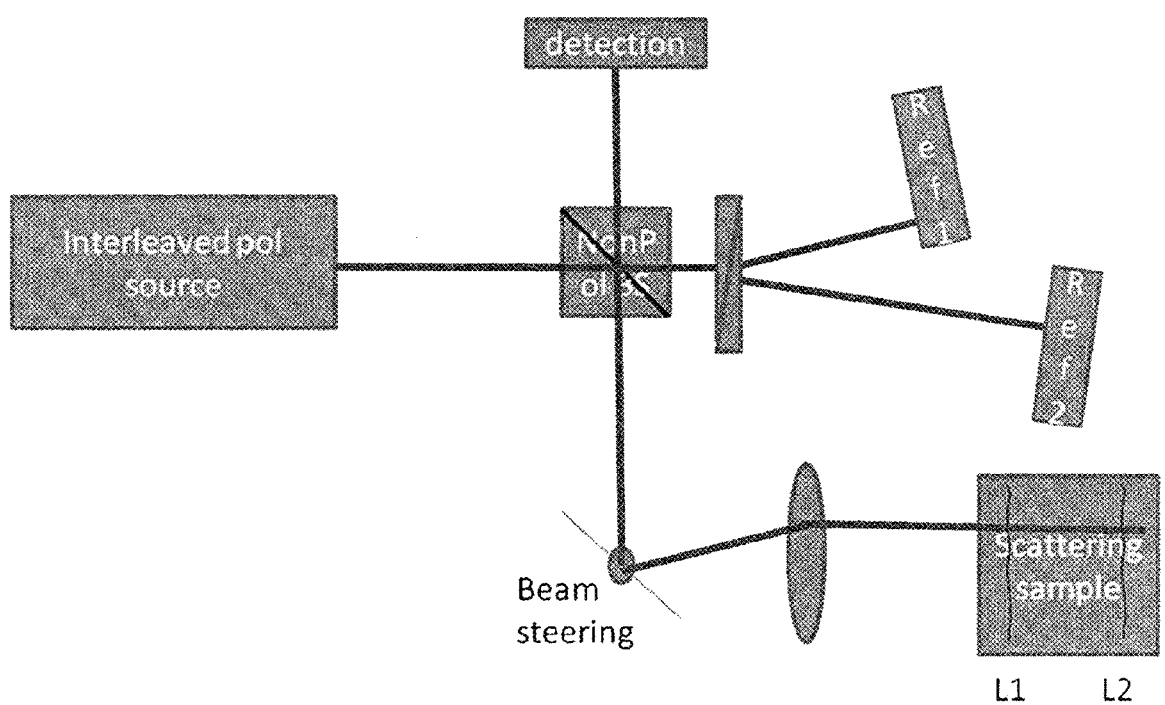

Sequential pulses of orthogonal polarization states are capable of introducing a periodic phase shift between sequential a-scans. A device may be placed in the difference path of the interferometer which causes light of one polarization to have a different path length or phase change than light of the orthogonal polarization as shown in FIG. 18. One example is shown in FIG. 18(a). An optical coherence tomography apparatus includes a source producing interleaved pulses of orthogonal polarization, sample and reference arms. A waveplate with its birefringent axis aligned parallel to one of the input polarizations introduces no polarization rotation, but does introduce a relatively fixed and precisely defined phase shift between the orthogonal polarizations. A small amount of tuning can be achieved by introducing a tilt to the waveplate. Materials may be chosen to control the amount of phase change introduced across the spectrum. For some applications it will be ideal to use an achromatic waveplate to introduce a constant phase shift across the spectrum. Alternatively as shown in FIG. 18(b) a polarization beamsplitter, such as a Wollaston prism, may split the reference beam path into two channels which may have arbitrarily widely adjustable phase differences.

Such a periodic phase shift may be used for the removal of complex conjugate artifact from frequency domain OCT. Introduction of a phase shift in the interference between adjacent a-scans provides the information necessary to remove the ambiguity between the positive and negative sides of the Fourier reconstruction of each a-scan. A specific implementation of this artifact removal utilizes the introduction of a 90 degree phase shift between adjacent a-scans. Computationally, the b-scan spectrum is Hilbert transformed in the spatial direction before calculation of the b-scan.

An arbitrarily long adjustable phase difference could be useful to simultaneously measure the position of two surfaces along the sample beam path which are separated by too great of a distance to be simultaneously viewable with a traditional measurement. The reference path of each respective polarization may be then set individually. The known separation between the two reference positions may be then included in a calculation of the distance between the two surfaces.

Polarization Sensitive Measurements

This section describes how the dual polarized swept-source systems of this invention can be useful in polarization-sensitive OCT (PS-OCT). As previously mentioned, the term dual-polarization swept source used herein means a laser generating sweeps with alternatively changing polarization states. It has one polarization state in odd sweeps and then switches to a different (orthogonal) polarization state in even sweeps.

Polarization-sensitive OCT (PS-OCT) is a functional extension of OCT that can measure the depth-resolved birefringent characteristics of biological tissues such as collagen, cartilage, and muscle. (See for example Hee et al "Polarization-sensitive low-coherence reflectometer for birefringence characterization and ranging", J. Opt. Soc. Am. B 9:903-908 1992, de Boer et al "Determination of the depth-resolved Stokes parameters of light backscattered from turbid media by use of polarization-sensitive optical coherence tomography," Opt. Lett. 24: 300-302 1999, and Hitzenberger et al "Measurement and imaging of birefringence and optic axis orientation by phase resolved polarization sensitive optical coherence tomography," Opt. Express 9: 780-790 2001). Since the round-trip nature of light propagation in OCT cancels the effect of any circular birefringence, biological samples were normally modeled as a linearly birefringent material in PS-OCT, meaning that the direction of the optic axis of the biological tissues is constrained to the QU-plane in a Poincare sphere representation.

In free-space PS-OCT systems, it was possible to measure tissue birefringence and optical axis orientation with a single A-scan acquisition. The sample was illuminated by an incident beam of light with circular polarization state, which was insensitive to the direction of the optic axis of the sample. The tissue birefringence and optics axis were measured by evaluating the OCT signal in two separate detection channels of orthogonal polarization states.

However, it is difficult to measure tissue birefringence and optic axis orientation with a single A-scan acquisition in a fiber-based PS-OCT system, since the fiber introduces a constant but unknown birefringence. The incident polarization state is no longer known and the overall direction of the optic axis from the combination of sample and fibers is no longer constrained to the QU-plane. It is possible that the polarization state incident on the sample becomes aligned parallel or orthogonal to the optic axis of the sample. Thus the incident polarization state remains unchanged upon reflection from the sample and carries no information regarding the sample polarization properties (see for example Park et al "In vivo burn depth determination by high-speed fiber-based polarization sensitive optical coherence tomography" J. Biomed. Opt. 6:474-479 2001). Use of at least two (or more) incident polarization states insure that at least one measurement carries useful polarization information and guarantees a measurement without ambiguity.

Embodiments of fiber-based polarization-sensitive OCT (PS-OCT) systems have been described in the prior art (See for example Saxer et al "High-speed fiber based polarization sensitive optical coherence tomography of in vivo human skin," Opt. Lett. 25:1355-1357 2000, Park et al "Real-time multi-functional optical coherence tomography," Opt. Express 11: 782-793 2003 and Park et al "Real-time fiber based multifunctional spectral-domain optical coherence tomography at 1.3 µm," Opt. Express 13: 3931-3944 2005). These methods have used expensive polarization modulators to achieve alternating polarization states for consecutive A-lines, which was required for an unambiguous polarization sensitive measurement.

Figure 19:
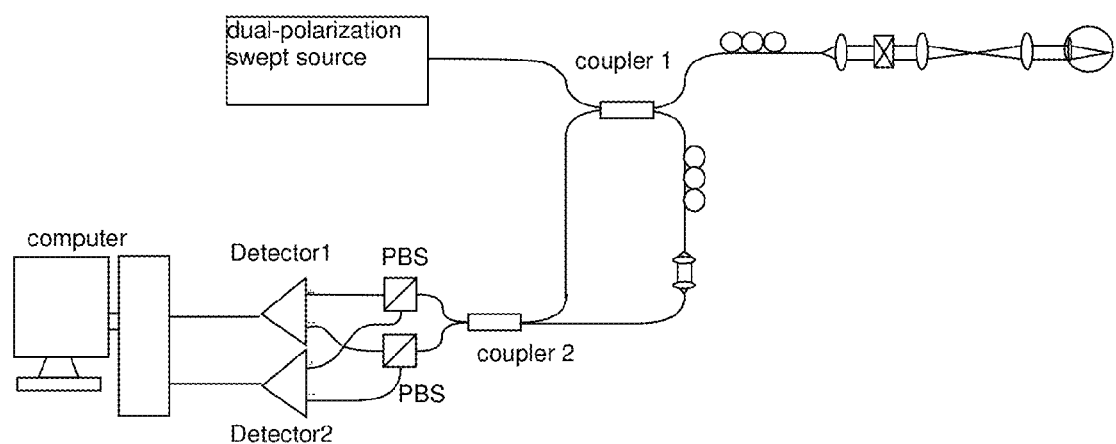
FIG. 19 shows an SS-OCT system capable of carrying out phase-sensitive measurements using a source capable of generating interleaved pulses of differing polarizations.

FIG. 19 shows a PS-OCT design with a dual-polarization swept source. While interleaved pulses of orthogonal linear polarizations would work for speckle reduction, phase shifting and temporal separating applications previously described, for PS-OCT, we prefer the two polarization states of the dual-polarization swept source that are orthogonal to each other in a Poincaré sphere representation. One example of this is one sweep linear polarized and the second sweep circular polarized. The fiber-optic based interferometer consists of two fused couplers. The light emitted from the swept source is coupled into coupler 1, which splits part of the light going to the sample arm and the remaining light going to the reference path. In the sample arm, the light reflected by the eye passes once again through the first coupler, which sends part of the light to coupler 2 (normally a 50/50 coupler), which combines 50% of light from the reference path and 50% from the sample path. Two polarization beam splitters (PBSs) are used to separate the signals of orthogonal polarization states and send them to two balanced detectors. The spectral signal from the two channels are digitized by a 12 bit commercially available digitizer, transformed from time to uniformly spaced wave number and then FFT transformed to retrieve the complex depth encoded signal in a workstation.

As the polarization sate of the input laser switches between two (or more) sweeps, (at least) two set of Stokes parameters can be obtained based on the complex depth encoded signal, i.e. the Stokes parameters for the $1^{st}$ polarization input (I1, Q1, U1, V1) and the second polarization input (I2, Q2, U2, V2). The intensity images are obtained from the average of I1 and I2. To determine the birefringence image, the detected signal reflected from the surface of the sample is adopted as the reference. The phase retardation is calculated by comparing the Stokes vectors between the surface and deeper axial position (See for example Saxer et al "High-speed fiber based polarization sensitive optical coherence tomography of in vivo human skin," Opt. Lett. 25: 1355-1357 2000).

Although various embodiments that incorporate the teachings of the present invention have been shown and described in detail herein, those skilled in the art can readily devise many other varied embodiments that still incorporate these teachings.

The following references are hereby incorporated by reference:

Patent Literature
U.S. Pat. No. 5,877,856
U.S. Pat. No. 5,892,583
U.S. Pat. No. 6,366,390
U.S. Pat. No. 6,847,449
U.S. Pat. No. 6,956,878
U.S. Pat. No. 7,126,693
U.S. Pat. No. 8,081,381
US Patent Publication No. 2010/0265467
US Patent Publication No. 2011/0080591
US Patent Publication No. 2011/0051148

Non-Patent Literature
Hee M R et al "Polarization-sensitive low-coherence reflectometer for birefringence characterization and ranging", J. Opt. Soc. Am. B 9:903-908 1992.
de Boer J F et al "Determination of the depth-resolved Stokes parameters of light backscattered from turbid media by use of polarization-sensitive optical coherence tomography," Opt. Lett. 24: 300-302 1999.
Hitzenberger C K et al "Measurement and imaging of birefringence and optic axis orientation by phase resolved polarization sensitive optical coherence tomography," Opt. Express 9:780-790 2001.
Park B H et al "In vivo burn depth determination by high-speed fiber-based polarization sensitive optical coherence tomography,"J. Biomed. Opt. 6: 474-479 2001.
Saxer C E et al "High-speed fiber based polarization sensitive optical coherence tomography of in vivo human skin," Opt. Lett. 25: 1355-1357 2000.
Park B H et al "Real-time multi-functional optical coherence tomography," Opt. Express 11:782-793 2003.
Park B et al "Real-time fiber based multifunctional spectral-domain optical coherence tomography at 1.3 µm," Opt. Express 13: 3931-3944 2005.
Goldberg B D et al "200 kHz A-line rate swept-source optical coherence tomography with a novel laser configuration" Proceedings of SPIE v.7889 paper 55 2011.
Potsaid B et al "Ultrahigh speed 1050 nm swept source/Fourier domain OCT retinal and anterior segment imaging at 100,000 to 400,000 axial scans per second," Opt. Express 18: 0029-20048 2010.
Yun S H et al "High-speed optical frequency-domain imaging" Opt. Express 11: 2953 2003.
Huber R et al "Amplified, frequency swept lasers for frequency domain reflectometry and OCT imaging: design and scaling principles" Opt. Express 13: 3513 2005.
Bilenca A et al "Numerical study of wavelength-swept semiconductor ring lasers: the role of refractive-index nonlinearities in semiconductor optical amplifiers and implications for biomedical imaging applications," Opt. Lett. 31: 760-762 2006.

Kuznetsov M et al "Compact Ultrafast Reflective Fabry-Perot Tunable Lasers for OCT Imaging Applications," Proc. SPIE 7554: 75541F 2010.

Yasuno Y et al "Simultaneous B-M-mode scanning method for real-time full-range Fourier domain optical coherence tomography," Appl. Opt. 45:1861-1865 2006.

Wang R K "In vivo full range complex Fourier domain optical coherence tomography," Appl. Phys. Lett. 90: 054103 2007.

Baumann B et al "Full range complex spectral domain optical coherence tomography without additional phase shifters," Opt. Express 15:13375-13387 2007.

Schmitt J M et al "Speckle in Optical Coherence Tomography", J. Biomed. Opt. 4:95 1999.

Huber R et al "Buffered Fourier domain mode locking: unidirectional swept laser sources for optical coherence tomography imaging at 370,000 lines/s," Opt. Lett. 31:2975-2977 2006.

Baumgartner A et al "Resolution-improved dual-beam and standard optical coherence tomography: a comparison" Graefes Arch Clin Exp Ophthalmol 238(5):385-92 2000.

Zotter S et al "Visualization of microvasculature by dual-beam phase-resolved Doppler optical coherence tomography" Opt Express 19(2):1217-27 2011.

Enock J "Dual reference arm low-coherence interferometer-based reflectometer for optical coherence tomography (OCT) application" Optics Communications 252(1-3): 202-211 2005.

Oh W Y et al "Wide tuning range wavelength-swept laser with two semiconductor optical amplifiers" IEEE Photonics Technology Letters 17(3): 678-680 2005.

Wang R K et al "Fourier domain optical coherence tomography achieves full range complex imaging in vivo by introducing a carrier frequency during scanning" Physics in Medicine and Biology 52(19): 5897 2007.

Vergnole S et al "Artifact removal in Fourier-domain optical coherence tomography with a piezoelectric fiber stretcher" Optics Letters 33(7): 732-734 2008.

Gotzinger E et al "High speed full range complex spectral domain optical coherence tomography" Optics Express 13(2): 583-594 2005.

Choma, M. A. et al. (2003). "Sensitivity Advantage of Swept Source and Fourier Domain Optical Coherence Tomography." *Optics Express* 2003 11(18): 2183-2189.

What is claimed is:

1. An optical coherence tomography (OCT) system comprising:
    a light source arranged to generate a beam of pulses of light, wherein the polarization state of the output pulses alternately switches between two orthogonally related states;
    a first beam divider for separating the pulse train along a sample arm and a reference arm;
    optics for scanning the pulse train in the sample arm over a set of transverse locations on a sample;
    a detector for measuring radiation returning from both the sample arm and the reference arm, the detector generating output signals in response thereto; and
    a processor for converting the output signals into image information and wherein said light source includes;
    an optical element located in the sample arm for selectively directing the pulses along one of two paths dependent upon the polarization state of the pulse so that the detector alternates between measuring radiation returning from one or the other of said two paths.

2. A system as recited in claim 1, wherein the optical element is configured so that the pulses of one polarization state are laterally displaced on the sample with respect to the pulses of the other polarization state.

3. A system as recited in claim 2, wherein the lateral displacement is selected to counteract the displacement of a constant velocity scan mechanism so that sequential A-scans occur in pairs that are substantially overlapping.

4. A system as recited in claim 2, wherein the lateral displacement is selected to facilitate a change measurement.

5. A system as recited in claim 2, wherein the lateral displacement is selected to compensate the effect of sample motion.

6. A system as recited in claim 2, wherein the detector is a balanced detector.

7. A method of generating images using an optical coherence tomography (OCT) system, said system include a light source arranged to generate a beam of pulses of light, said system further including a first beam divider for separating the pulse train along a sample arm and a reference arm and optics for scanning the pulse train in the sample arm over a set of transverse locations on a sample, said system including a detector for measuring radiation returning from both the sample arm and the reference arm, the detector generating output signals in response thereto, said system further including a processor for converting the output signals into image information, said method comprising:
    alternately switching the polarization state of the light pulses between two orthogonally related states; and
    selectively directing the pulses along one of two paths in the sample arm dependent upon the polarization state of the pulse so that the detector alternates measuring radiation returning from one or the other of said two paths.

8. A method as recited in claim 7 wherein pulses are selectively directed in a manner so that the pulses of one polarization state are laterally displaced on the sample with respect to the pulses of the other polarization state.

9. A method as recited in claim 8, wherein the lateral displacement is selected to counteract the displacement of a constant velocity scan mechanism so that sequential A-scans occur in pairs that are substantially overlapping.

10. A method as recited in claim 8, wherein the lateral displacement is selected to facilitate a change measurement.

11. A method as recited in claim 8, wherein the lateral displacement is selected to compensate the effect of sample motion.

* * * * *

UNITED STATES PATENT AND TRADEMARK OFFICE
CERTIFICATE OF CORRECTION

PATENT NO. : 8,908,189 B2  
APPLICATION NO. : 13/444410  
DATED : December 9, 2014  
INVENTOR(S) : Alexandre R. Tumlinson Page 1 of 1

It is certified that error appears in the above-identified patent and that said Letters Patent is hereby corrected as shown below:

In the Specification

In column 1, line 65, delete "2006)" and insert -- 2006). --, therefor.

In column 3, line 23, delete "and or" and insert -- and/or --, therefor.

In column 5, line 45, delete "minor" and insert -- mirror --, therefor.

In column 7, line 27, delete "minors." and insert -- mirrors. --, therefor.

In column 10, line 12, delete "minors" and insert -- mirrors --, therefor.

In column 10, line 17, delete "minor," and insert -- mirror, --, therefor.

In column 16, line 42, delete "tomography,"J." and insert -- tomography, "J. --, therefor.

Signed and Sealed this  
Fourteenth Day of April, 2015

Michelle K. Lee  
*Director of the United States Patent and Trademark Office*